United States Patent [19]

Andersson et al.

[11] Patent Number: 5,215,979

[45] Date of Patent: Jun. 1, 1993

[54] 16,17-ACETALSUBSTITUTED PREGNANE 21-OIC ACID DERIVATIVES

[75] Inventors: Paul H. Andersson, Södra Sandby; Per T. Andersson, Lund; Bengt I. Axelsson, Genarp; Ralph L. Brattsand, Lund; Bror A. Thalen, Bjärred; Jan W. Trofast, Lund, all of Sweden

[73] Assignee: Aktiebolaget Draco, Sweden

[21] Appl. No.: 776,874

[22] Filed: Oct. 16, 1991

Related U.S. Application Data

[63] Continuation of Ser. No. 530,463, May 29, 1990, abandoned, which is a continuation of Ser. No. 938,811, Dec. 8, 1986, abandoned.

[30] Foreign Application Priority Data

Dec. 19, 1985 [SE] Sweden ................ 8506015

[51] Int. Cl.$^5$ ............ A61K 31/58; A61K 31/56; A61K 31/385; C07J 71/00
[52] U.S. Cl. ............ 514/172; 514/177; 514/463; 514/826; 514/859; 514/861; 514/863; 514/886; 540/61; 540/70
[58] Field of Search ......... 514/463, 172, 179, 826, 514/859, 861, 863, 886; 549/432; 540/70, 61

[56] References Cited

U.S. PATENT DOCUMENTS

| | | | |
|---|---|---|---|
| 3,824,260 | 7/1974 | Laurent et al. | 260/397.1 |
| 3,875,194 | 4/1975 | Laurent et al. | 260/397.1 |
| 3,919,421 | 11/1975 | Laurent et al. | 260/174 |
| 3,956,347 | 5/1976 | Laurent et al. | 260/397.1 |
| 4,257,969 | 3/1981 | Varma | 2690/397.1 |

FOREIGN PATENT DOCUMENTS

| | | |
|---|---|---|
| 2204361 | 8/1973 | Fed. Rep. of Germany . |
| 2360444 | 6/1975 | Fed. Rep. of Germany . |
| 2513557 | 9/1976 | Fed. Rep. of Germany . |
| 2513555 | 12/1976 | Fed. Rep. of Germany . |
| 378109 | 8/1975 | Sweden . |
| 402111 | 6/1978 | Sweden . |
| 1387911 | 3/1975 | United Kingdom . |
| 1479488 | 7/1977 | United Kingdom . |

OTHER PUBLICATIONS

R. Brattsand, et al., European Journal of Respiratory Diseases, Supp. No. 126, vol. 64, p. 513 (1983).

(List continued on next page.)

Primary Examiner—John W. Rollins
Attorney, Agent, or Firm—White & Case

[57] ABSTRACT

The invention refers to compounds having activity against inflammatory, allergic, and dermatological conditions. The compounds are characterized by the formula

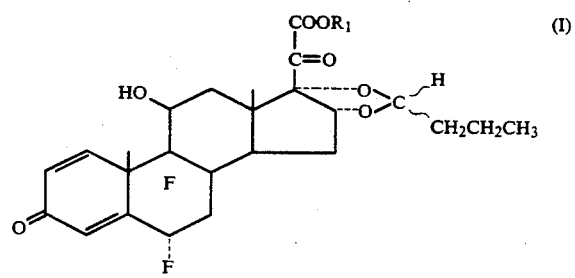

or a stereoisomeric component thereof, in which formula $R_1$ is selected from a straight or branched hydrocarbon chain having 1–4 carbon atoms.

The invention also refers to processes for the preparation of these compounds, pharmaceutical preparations containing one of the compounds and a method for the treatment of inflammatory, allergic, muscoskeletal and dermatological conditions.

10 Claims, No Drawings

OTHER PUBLICATIONS

R. Brattsand, et al. and M. Willen et al., Microcirculation: Technical and Experimental, vol. 5 Nos. 2–3, Abstracts M-190 and M-191, p. 263 (1986).

R. Brattsand, et al in "Determinants of the lung-specific actions of Glucocorticosteroids," pp. 145–153 (1984).

C. G. A. Persson, Lung, vol. 166, pp. 1–23 (1988).

S. M. Laycock et al., International Journal of Allergy and Applied Immunology vol. 81, pp. 363–367 (1986).

S. M. Laycock et al., International Journal of Allergy and Applied Immunology vol. 82, pp. 347–348 (1987).

H. Smith, Pulmonary Pharmacology, vol. 2, pp. 59–74, 1989.

H. Laurent et al, "New Biologically Active Pregnan-2-1-OIC Acid Esters", I. Steroid Biochem. 6 (1975) pp. 185–192.

Goodman and Gilman's *The Pharmacological Basis of Therpeutics, Seventh Edition*, pp. 5–15, 21, 44–47, 1475, (1985).

16,17-ACETALSUBSTITUTED PREGNANE 21-OIC ACID DERIVATIVES

This application is a continuation of application Ser. No. 07/530,463, filed on May 29, 1990, now abandoned, which is a continuation of application Ser. No. 06/938,811 filed on Dec, 8, 1986, now abandoned.

DESCRIPTION

1. Field of the Invention

The present invention relates to novel, pharmacologically active compounds and to processes for their preparation. The invention also relates to pharmaceutical compositions containing the compounds and to methods of treatment of inflammatory, allergic, or dermatological conditions with these compounds.

The object of the invention is to provide a glucocorticosteroid which possesses high anti-inflammatory potency at the place of application and low glucocorticoid systemic potency.

2. Background Art

Glucocorticosteroids (GCS) are the most valuable drugs for relief of asthma and thinitis. It is widely accepted that GCS exert their therapeutic efficacy by anti-inflammatory and anti-anaphylactic actions within airway and lung tissue. The long term oral use of GCS is greatly hampered by severe side effects outside the lung region. Accordingly, only a minor part of patients with asthma or rhinitis currently undergo oral GCS therapy. A better safety can be reached by delivering GCS by inhalation of aerosol preparations. However, also the potent inhaled GCS in current side clinical use—beclomethasone $17\alpha$, 21-dipropionate and budesonide—have a rather narrow safety margin and for both unwanted GCS actions within the general circulation have been reported with the highest of the recommended doses for inhalation (C.-G. Löfdahl, T. Mellstrand and N. Svedmyr, Eur. J. Respir. Dis. Suppl 136, 65 (1984), 69: S.-A. Johansson, K.-E. Andersson, R. Brattand, E. Gruvstad and P. Hedner, Eur. J. Clin. Pharmacol. 22 (1982), 523: J. H. Toogood, J. C. Baskerville, B. Jennings, N. M. Lefcoe and S.-A. Johansson. J. Allergy Clin. Immunol. 70 (1982), 288). This may be related to that such compounds after absorption have a plasma half life of $\geq 2$ h and are inactivated mainly in the liver (R. Pauwels and M. van der Straeten, Eur. J. Respir. Dis. Suppl 122, 63 (1982), 83: A. Ryrfeldt, P. Andersson, S. Edsbäcker, M. Tönnesson, D. Davies and R. Pauwels, Eur. J. Respir. Dis. Supp 122, 63 (1982), 86). In accordance with this, budesonide shows a low selectivity for the application within airways in a model system (R. Brattsand, L. Källström. U. Johansson and M. Dahlbäck in Glucocorticosteroids Inflammation and Bronchial Hyperreactivity, Editor J. C. Hogg, R. Elliel-Micallef, R. Brattsand, Excerpta Medica 1985, Amsterdam, pp 150-153). Recently GCS of other chemical structures, e.g. fluocortin butyl ester (FCB) have been described in experimental systems (J.-F. Kapp, H. Koch, M. Töpert, H. J. Kessler and E. Gerhards. Arzneim.-Forsch. 27 (1977), 2230). These compounds have the potential to be inactivated by biotransformation by hydrolysis also outside the liver, but as studied by Mützel (Arzeim.-Forsch. 27 (1977), 2191) FCB has as long half life time in plasma as budesonide. According to a lower potency, FCB must be used in much higher doses than budesonide or BDP (P. S. Burge, J. Efthimiou, M. Turner-Warwich and P. T. J. Nelmes, Clinical Allergy 12 (1982), 523).

One object of the invention is to describe new GCS compounds to be used by inhalation. They are characterized by reasonable anti-inflammatory and anti-anaphylactic potency at the application site within airways and particularly they have a markedly improved relationship between that potency and the activity to provoke GCS actions outside the treated region.

DISCLOSURE OF THE INVENTION

The present invention is based on the observation that certain pregnanoic acid esters possess high anti-inflammatory and anti-anaphylactic potency at the place of application but in combination with only low glucocorticoid systemic effects. The compounds of the invention can be used for the treatment and control of inflammatory, allergic or immunologic diseases in the respiratory airways, in the skin, in joints or in the bowel.

The compounds of the invention are characterized by the formula

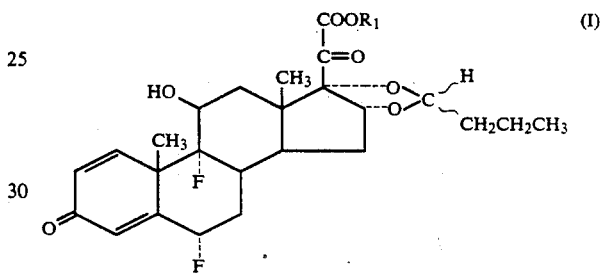

or a stereoisomeric component thereof, in which formula $R_1$ is selected from a straight or branched hydrocarbon chain having 1-4 carbon atoms.

Particularly preferred $R_1$-substituents are methyl, ethyl, n-propyl, isopropyl, n-butyl, isobutyl and sec.-butyl.

The individual stereoisomeric components present in a mixture of a steroic having the above formula (1) can be elucidated in the following way:

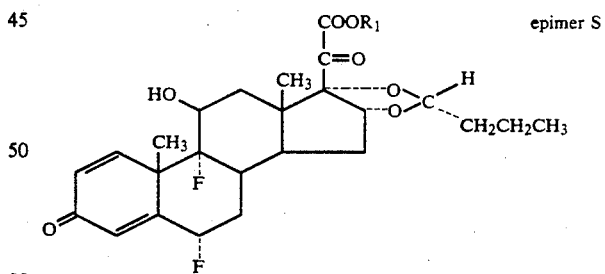

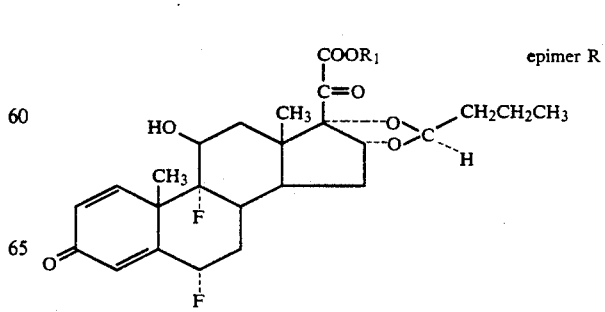

The preferred epimer is the 22 R-isomer.

METHODS OF PREPARATION

A. Oxidation of an aldehyde of the formula

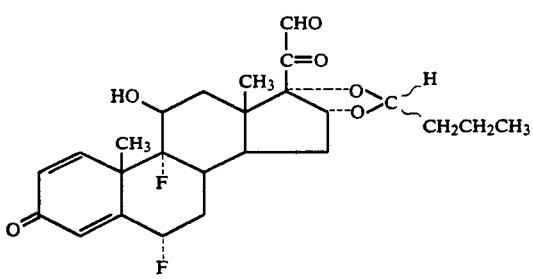

(II)

or its hydrate or hemiacetals in the presence of cyanide ions and an alcohol of the formula $R_1-OH$ where $R_1$ has the meaning given above.

The process according to this method is described below in conjunction with the preceding step to prepare the compound of the formula II.

In the preceding step a 21-hydroxy steroid of the formula

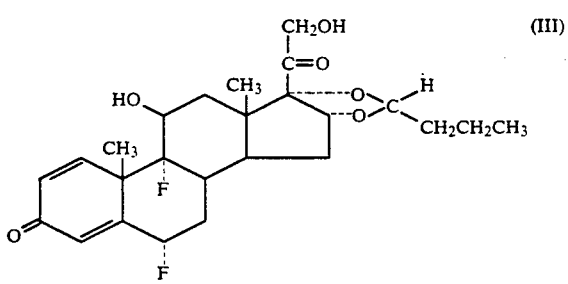

(III)

is converted using oxygen (or air) and a catalyst such as a copper (II) salt in an alcohol solution, to the steroid aldehyd of formula II.

Suitable copper (II) salts for this reaction are water soluble salts of inorganic or organic acids. Suitable copper(II) salts include but are not limited to copper (II) format, copper (II) acetate, copper (II) propionate or copper (II) butyrate.

Alcohols usable in the first reaction step are alcohols of the general formula $R_1OH$, wherein $R_1$ has the same meanings as in formula I. Especially preferred alcohols are methanol, ethanol, propanol, isopropanol, butanol, isobutanol or sec.-butanol.

The preceding reaction step is preferably accomplished at a reaction temperature of 0° C. to 40° C. The reaction time, dependent on the reaction temperature, is 5-60 minutes preferably 40 minutes at room temperature.

Depending on whether aqueous or anhydrous alcohols are utilized for the reaction, the corresponding hydrate, hemiacetals or mixtures thereof are formed during this reaction. The nature of the resultant product is important with respect to the subsequent reaction. The same alcohol shall preferably be used as in the second reaction step.

The acetal or hemiacetal derivatives of the aldehyde of formula II can be converted directly into the pregnanoic acid esters of the general formula I by oxidation. The alcohol corresponding to the ester, which is desired, shall be used in the acetalization step. The oxidation is performed with hypochlorous acid generated from an alkali hypochlorite, e.g. sodium or potassium hypochlorite, and an acid preferably acetic acid, at a temperature of 0°-25° C., preferably at 0° C. Suitable solvents are ketones, e.g. acetone, methyl ethyl ketone, and alcohols. The same alcohol shall be used as is desired as part of the carboxylic acid ester.

The conversion of the steroid aldehyde of formula II into the pregnanoic acid esters of the general formula I can be accomplished with the aid of a variety of oxidizing agents.

For example, it is possible to convert II or its addition compounds to the pregnanoic acid esters with alcohols and organic oxidizing agents, such as ammonium persulfate, N-bromosuccinimide, 5,6-dichloro-2,3-dicyanobenzoquinone or triphenyltetrazolium chloride.

It is also possible to oxidize the steroid aldehyde II with oxidizing metallic ozides or metallic salts, such as manganese oxide, silver oxide, chromic acid, permanganate and similar in the presence of alcohols and optionally of acids. The steroid aldehyde II can also be reacted with atmospheric oxygen in the presence of an alcohol and cyanide ions.

When a 20-keto-21-oic acid is obtained by the process A, the acid is converted to the ester of formula I for instance according to method C.

The most rapid reaction and the highest yields are obtained when oxidizing heavy metal oxides are used in the presence of alcohol and cyanide ions. The second process step shall be accomplished with the use of the alcohol intended as part of the ester function and also used in the first reaction step. If another alcohol is utilized in the first reaction step, the ester with this alcohol will be obtained as impurity in the product from the reaction from the aldehyde II to the ester I, as this alcohol is introduced to the second reaction step via the aldehyde hemiacetal. Excess alcohol can also be used simultaneously as the reaction solvent, although it is of course also possible to admix inert solvents to the reaction mixture in addition to the alcohols. Suitable inert solvents but are not limited to hydrocarbons, e.g. benzene, cyclohexane or soluene: chlorinated hydrocarbons, e.g. methylene chloride, chloroform or tetrachloroethane; ethers, e.g. diethyl ether, diisopropyl ether, dibutyl ether, glycol dimethyl ether, dioxane or tetrahydrofurane: dipolar aprotic solvents, e.g. dimethylformamide, N-methylacetamide or N-methylpyrrolidone; etc.

For the second reaction step suitable oxides include but are not limited to silver oxides, lead (IV) oxide, minimum ($Pb_3O_4$), vanadium (V) oxide or manganese (IV) oxide. The catalyst employed for this reaction step is cyanide ions, preferably obtained from alkali metal cyanides, e.g. sodium or potassium cyanide. If alkali cyanides are utilized as the reagents yielding cyanide ions, the reaction is suitable conducted by adding to the reaction mixture an alkali neutralizing amount of acid, e.g. mineral acid such as sulfuric, phosphoric or hydrochloric acid; sulfonic acid such as p-toluenesulfonic acid; or carboxylic acid such as formic or acetic acid to maintain the pH at about 2.0 to 6.0.

The reaction is suitably conducted at a reaction temperature between 0° C. and +50° C., preferably at room temperature. The reaction time, dependent on the temperature, is 15 to 120 minutes, preferably 50 minutes at room temperature.

If the above described reaction is allowed to proceed for an extended period of time, e.g. more than 48 hours, the major product will be the 20-hydroxy-21-carboxylic acid ester having the formula mentioned in method B below.

B. Oxidation of the 20-hydroxy group of the compound of the formula

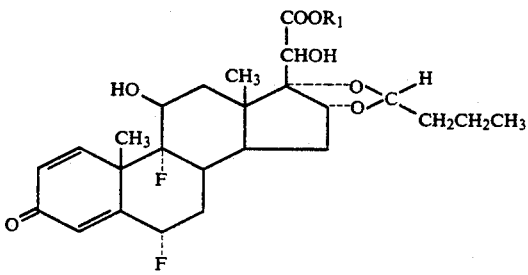

The 20-hydroxy group can be in the α- or β-position and the process is performed in an inert solvent with an oxidizing metal oxide or metallic salt.

The process of this invention according to method B can be conducted in an inert solvent. Suitable solvents are hydrocarbons, e.g. cyclohexane, benzene, soluene and xylene; chlorinated hydrocarbons, e.g. methylene chloride, chloroform, carbon tetrachloride; ethers, e.g. diethyl ether, diisopropyl ether, dibutyl ether, tetrahydrofuran, dioxane, glycol dimethyl ether; ketones, e.g. acetone, methyl ethyl ketone, methyl isobutyl ketone; and alcohols, e.g. methanol, ethanol, isopropanol and tert.-butanol; and mixtures of these solvents.

The oxidation according to method B can be conducted using manganese (IV) oxide, lead (IV) oxide or lead (IV) acetate. In order to obtain high yields in this process active manganese (IV) oxide is preferably employed.

The oxidation is preferably effected at a reaction temperature between 0° C. and 150° C. Thus, it is possible to perform the oxidation according to method B at room temperature or at the boiling temperature of the solvent employed.

The configuration of the 20-hydroxy group of the starting compound is of no significance in the process of the invention. Therefore, both the 20α- and 20β-hydroxy epimers as well as their mixtures can be oxidized to the pregnanoic acid derivatives of the general formula I.

C. Esterification of a carboxylic acid of formula

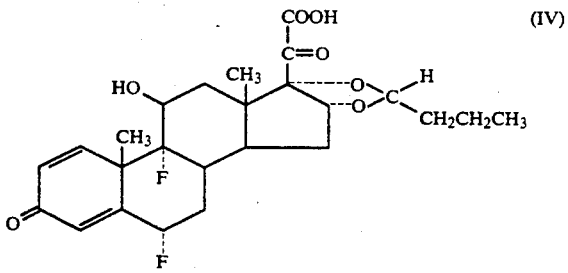

or a functionally equivalent derivative thereof with a compound of the formula $R_1$—OH or a functionally derivative thereof, wherein $R_1$ has the meaning given above.

The compound of formula IV is obtained by oxidation of the aldehyd II or a hydrate or hemiacetal thereof, with an oxidizing agent.

The 20-keto-21-oic acids used in the process of this invention according to method C can be prepared by oxidation of a compound of the general formula II with a oxidizing metallic oxide preferably silver oxide freshly prepared from silver nitrate and an alkali hydrocide, e.g. sodium or potassium hydroxide in water solution. Other usable oxidizing reagents include tetrabutylammonium permanganate, silver (II) complexes, chlorite and the like.

Alternatively, the cyanohydrine derivative of II can be oxidized with methylene blue or with metallic oxides, such as manganese oxide or silver oxide.

The 20-keto-21-oic acids can also be prepared by saponification of the 21-esters of formula I ($R_1$=alkyl). The saponification can be conducted with conventional techniques, e.g. by saponification of the esters in water or an aqueous alcohol in the presence of an acidic catalyst, e.g. hydrochloric acid, sulfuric acid or p-toluenesulfonic acid or in the presence of a basic catalyst, e.g. potassium hydrogen carbonate, potassium carbonate, sodium or potassium hydroxide.

The esterification of the free acids of formula IV is conducted by conventional techniques. Thus, the free acids can be reacted with an aliphatic $C_1$–$C_4$ diazo compound for example, with diazomethane or diazoethane, producing the corresponding methyl and ethyl ester, respectively. A generally applicable method is the reaction of the free acids with an alcohol in the presence of N,N'-carbonyl diimidazole, dicyclohexyl carbodiimide, anion exchange resins, polymer-protected $AlCl_3$, pyridinium salts, $H_3BO_3$—$H_2SO_4$, $BF_3$ $Et_2O$, molecular sieves—$H_2SO_4$, 1,1'-(carbonyldioxy)dibenzotriazole, 6-chloro-1-p-chlorobenzene sulfonyloxybenzotriazole, trifluoroacetic acid anhydride, phase-transfer catalysts, trimethylchlorosilane, N,N-bis(2-oxo-3-oxazolidinyl)-phosphordiamidic chloride and the like. The acids can also be converted to a mixed anhydride, e.g. with isobutyl chlorocarbonate, and reacted with the selected alcohol, or to the silver salts, the latter reacted with an alkyl halogenide.

Alternatively, a salt of the 20-keto-21-oic acid with an alkali metal, e.g. lithium, sodium or potassium, a salt of an amine, e.g. triethyl- or tributylamine, a salt of a bicyclic amidine, e.g. 1,5-diazabicyclo[5.4.0] undecene-5(DBU), a salt of a quarternary ammonium compound such as a salt of tetrabutylammonium or tricaprylmethylammonium, may be reacted with an appropriate alkylating agent, for example an alkyl halide or dialkylsulfate, e.g. dimethyl- or diethylsulfate, preferably in a polar solvent medium such as acetone, methyl ethyl detone, dimethyl formamide, dimethyl sulphoxide, methylene chloride or chloroform, conveniently at a temperature in the range 25°–100° C. The reaction may also be performed in the presence of a crown ether.

Another method of producing the ester of formula I is by converting the free acids into the corresponding dimethylformamide alkyl acetals. The free acids can also be reacted in the presence of a strong acidic catalyst, e.g. hydrogen chloride, sulfuric acid, perchloric acid, trifluoromethylsulfonic acid or p-toluenesulfonic acid, with an alcohol or with a lower alkane-carboxylic acid ester of the selected alcohol. The free carboxylic acids can also be converted into their acid chloride or acid anhydride and reacted with the selected alcohols in the presence of basic catalysts.

D. Transesterification of an ester of the formula

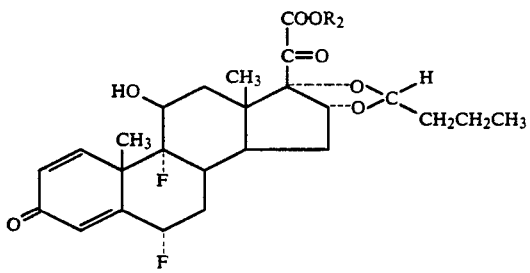

wherein $R_2$ is methyl or ethyl with an alcohol of the formula $R_1$—OH wherein $R_1$ has the meaning given above.

The transesterification is preferably performed in the presence of acidic or a basic catalyst.

The process of this invention according to method D is conducted by reacting the esters of the formula above with the desired alcohol of the formula $R_1OH$ in the presence of a preferably acidic or anhydrous basic catalyst.

Preferred basic catalysts employed are alkali, alkaline earth and aluminum alcoholates and preferred acidic catalyst is p-toluenesulphonic acid. The reaction is preferably conducted at a reaction temperature of between 0° C. and 180° C. During this reaction, the alcohol is employed in excess. The alcohol can also be diluted with an inert solvent. Suitable solvents are ethers, e.g. di-n-butyl ether, tetrahydrofuran, dioxane and glycol dimethyl ether; or dipolar aprotic solvents, e.g. dimethylformamide N-methylacetamide, dimethyl sulfoxide, N-methylpyrrolidone and acetonitrile.

As esters of the formula above for the process of method D lower alkyl esters are preferably used, e.g. the methyl or ethyl ester of the pregnanoic acid.

Common to methods A-D is the circumstance that any process may as starting material use a C-22 epimeric mixture which, if desired, after the completion of the process is resolved into its R and S isomers (C-22). Alternatively, any process A-D may be performed by using as starting material an R or S isomer, in which case the process results in the obtaining of the end products in the form of an R or S isomer, respectively.

PHARMACEUTICAL PREPARATIONS

The compounds of the invention may be used for different modes of local administration dependent on the site of inflammation, e.g. percutaneously, parenterally or for local administration in the respiratory tract by inhalation. An important aim of the formulation design is to reach optimal bioavailability of the active steroid ingredient. For percutaneous formulations this is advantageously achieved if the steroid is dissolved with a high therodynamic activity in the vehicle. This is attained by using a suitable system or solvents comprising suitable glycols, such as propylene glycol or 1,3-butandiol either as such or in combination with water.

It is also possible to dissolve the steroid either completely or partially in a lipophilic phase with the aid of a surfactant as a solubilizer. The percutaneous compositions can be an ointment, an oil in water cream, a water in oil cream or a lotion. In the emulsion vehicles the system comprising the dissolved active component can make up the disperse phase as well as the continuous one. The steroid can also exist in the above compositions as a micronized, solid substance.

Pressurized aerosols for steroids are intended for oral or nasal inhalation. The aerosol system is designed in such a way that each delivered dose contains 10–1000 μg, preferably 20–250 μg of the active steroid. The most active steroids are administered in the lower part of the dose range. The micronized steroid consists of particles substantially smaller than 5 μm, which are suspended in a propellent mixture with the assistance of a dispersant, such as sorbitan trioleate, oleic acid, lecithin or sodium salt of dioctylsulphosuccinic acid.

The micronized steroid can also be mixed with a carrier substance such as lactose or glucose. The powder mixture is dispensed into hard gelatin capsules, each containing the desired dose of the steroid. At use, the capsule is placed in a powder inhaler device and the dose of the powder is inhaled into the airways.

WORKING EXAMPLES

The invention will be further illustrated by the following non-limitative examples. In the examples a flow-rate of 2.5 ml/$cm^2 \times h^{-1}$ is used at the preparative chromatographic runs. Molecular weights are in all examples determined with electron impact mass spectrometry and the melting points on a Leitz Wetzlar hot stage microscope. All HPLC analyses (HPLC=High Performance Liquid Chromatography) were performed on a Waters μBondapak $C_{18}$ column (300×3.9 mm internal diameter) with a flowrate of 1.0 ml/min and with ethanol-water in ratios between 50:50 and 60:40 as mobile phase, if not otherwise stated.

EXAMPLE 1

A solution of 0.18 g of copper (II) acetate in 100 ml of methanol was added to a solution of 0.825 g of (22R)-16α, 17α-butylidenedioxy-6α,9α-difluoro-11β, 21-dihydroxypregna-1,4-diene-3,20-dione in 50 ml of methanol. Air was bubbled through the reaction mixture for 40 min. at room temperature. Most of the methanol was removed and the residue dissolved in 150 ml of methylene chloride, washed with 10% aqueous ammonium chloride and water and dried. The residue after evaporation was precipitated from methylene chloride—petroleum ether leaving 0.837 g of (22R)-16α,17α-butylidenedioxy-6α,9α-difluoro-11β-hydroxy-3,20-dioxopregna-1, 4-diene-21-al methyl hemiacetal. The purity determined by HPLC was 98.5%.

100 mg of this aldehyde was dissolved in 1.25 ml of dimethylformamide. Potassium cyanide (13 mg) manganese (IV) oxide (175 mg), methanol (0.5 ml) and conc. acetic acid (0.1 ml) was added and the reaction mixture was stirred for 50 min at room temperature. The manganese (IV) oxide was removed moved by filtration and 25 ml of methylene chloride was added to the filtrate. The solution was washed with 5% aqueous potassium carbonate and water. After drying the solvents were evaporated and the residue recrystallized from acetone—water yielding 66 mg of methyl (22R)-16α,17α-butylidenedioxy-6α, 9α-difluoro-11β-hydroxy-3,20-dioxopregna-1,4-diene-21-oate. The purity determined by HPLC was 94.7%. Melting point: 225°–36° C. $[\alpha]D25 = +72.0°$ (c=0.400; $CH_2Cl_2$). The molecular weight was 494.

EXAMPLE 2

Copper (II) acetate (0.5 g) was added to a solution of 1 g of (22R)-16α,17α-butylidenedioxy-6α,9α-difluoro-11β,21-dihydroxypregna1,4-diene-3,20-dione in 200 ml of methanol. The mixture was stirred 3 days at room temperature. Oxygen was introduced for 3 h and the mixture was stirred for another 8 days. The solvent was evaporated and the residue was dissolved in 300 ml of methylene chloride washed with 4×25 ml of 10% ammonium hydroxide, 2×25 ml of water, dried and evaporated. The residue was purified by chromatography on a Sephadex LH-20 column (72×6.3 cm) using chloroform as mobile phase. The fractions 2550-3000 ml (A) and 3150-3825 ml (B) were collected and evaporated. From A was 102 mg of a solid obtained, identified as methyl (22R)-16α, 17α-butylidene-dioxy-6α,9α-difluoro-11β-hydroxy-3, 20-dioxopregna-1,4-diene-21-oate and from B was 586 mg of methyl (22R)-16α,17α-butylidenedioxy-6α,9α-difluoro-11β, 20-dihydroxy-3-oxopregna-1,4-diene-21-oate isolated and identified.

To a solution of 100 mg of the latter compound 200 mg of manganese (IV) oxide was added and the reaction mixture as stirred for 16 h at room temperature. The manganese (IV) dioxide was removed by filtration through Celite and the solvent was evaporated. The residue was dissolved in chloroform and chromatographed on a Sephadex LH-20 column (72×6.3 cm) using chloroform as mobile phase. The fraction 2190-2560 ml was collected, evaporated and rechromatographed on a Sephanex LH-20 column (72×6.3 cm) using heptane:chloroform:ethanol, 20:20:1, as mobile phase. The fraction 5130-5745 ml was collected and evaporated yielding 35 mg of methyl (22R)-16α,17α-butylidenedioxy-6α,9α-difluoro-11β-hydroxy-3,20-dioxopregna-1, 4-diene-21-oate. The purity determined by HPLC was 95.5%. Melting point: 223°-35° C. The molecular weight was 494.

EXAMPLE 3

A solution of 0.45 g of copper (II) acetate in 100 ml of absolute ethanol was added to solution of 2.0 g of (22R)-16α,17α-butylidenedioxy-6α,9α-difluoro-11β, 21-dihydroxypregna-1,4-diene-3,20-dione in 300 ml of absolute ethanol as reacted and the product isolated as described in Example 1 yielding 2.0 g of (22R)-16α,17α-butylidenedioxy-6α, 9α-difluoro-11β-hydroxy-3,20-dioxopregna-1,4-diene-21-al ethyl hemiacetal.

This aldehyde was reacted under the conditions described in Example 1 changing methanol for ethanol. Yield: 1.77 g of crude product which was purified on a Sephadex LH-20 column (76.5×6.3 cm) using heptane:chloroform:ethanol, 20:20:1, as mobile phase. The fraction 2655-3150 ml was collected and evaporated. After recrystallization of the residue from ethanol, 1.03 g of ethyl (22R)-16α,17α-butylidenedioxy-6α,9α-difluoro-11β-hydroxy-3, 20-dioxopregna-1,4-diene-21-oate was obtained. The purity determined by HPLC was 97%. Melting point: 227°-35° C. [α]D25= +67.2° (c=0.180; CH2Cl2). The molecular weight was 508.

EXAMPLE 4

A solution of 0.35 g of copper (II) acetate in 150 ml of propanol was added to a solution of 0.80 g of (22R)-16α,17α-butylidenedioxy-6α,9α-difluoro-11β, 21-dihydroxypregna-1,4-diene-3,20-dione in 100 ml of propanol was reacted and the produced isolated as described in Example 1 yielding 0.95 g of (22R)-16α,17α-butylidenedioxy-6α,9α-difluoro-11β-hydroxy-3, 20-dioxopregna-1,4-diene-21-al propyl hemiacetal.

This aldehyde was reacted under the conditions described in Example 1 changing methanol for propanol. The crude product was purified on Sephadex LH-20 column (76.5×6.3 cm) using heptane:chloroform:ethanol, 20:20:1, as mobile phase. The fraction 3450-3990 ml was collected and evaporated. The residue was precipitated from methylene chloride—petroleum ether yielding 0.38 g of n-propyl (22R)-16α,17α-butylidenedioxy-6α,9α-difluoro-11β-hydroxy-3, 20-dioxopregna-1,4-diene-21-oate. The purity determined by HPLC was 98.9%. Melting point: 192°-195° C. [α]D25= +66.4° (c=0.256; CH2Cl2). The molecular weight was 522.

EXAMPLE 5

A solution of 0.45 g of copper (II) acetate in 150 ml of methanol as added to a solution of 1.0 g of (22R)-16α,17α-butylidenedioxy-6α,9α-difluoro-11β, 21-dihydroxypregna-1,4-diene-3,20-dione in 150 ml of methanol was reacted and the product isolated as described in Example 1. The product was dissolved in 15 ml of isopropanol and evaporated. This procedure was repeated twice leaving 1.2 g of (22R)-16α,17α-butylidenedioxy-6α, 9α-difluoro-11β-hydroxy-3,20-dioxopregna-1,4-diene-21-al propyl hemiacetal.

The aldehyde was reacted under the conditions described in Example 1 changing methanol for isopropanol. The crude product was purified on a Sephadex LH-20 column (71.5×6.3 cm) using chloroform as mobile phase. The fraction 1845-2100 ml was collected the evaporated leaving 0.42 g of a solid which was precipitated from methylene chloride—petroleum ether. Yield: 0.41 g of isopropyl (22R)-16α,17α-butylidenedioxy-6α,-9α-difluoro-11β-hydroxy-3, 20-dioxopregna-1,4-diene-21-oate. The purity determined by HPLC was 96.5%. Melting point: 198°-210° C. [α]D25= +62.0° (0.292; CH2Cl2). The molecular weight was 522.

EXAMPLE 6

A solution of 55 mg of copper (II) acetate in 25 ml of methanol was added to a solution of 200 mg of (22R)-16α,17α-butylidenedioxy-6α,9α-difluoro-11β, 21-dihydroxypregna-1,4-diene-3,20-dione in 25 ml of methanol was reacted and the product isolated as described in Example 1 yielding 250 mg of (22R)-16α,17α-butylidenedioxy-6α,9α-difluoro-11β-hydroxy-3,20-dioxopregna-1, 4-diene-21-al methyl hemiacetal.

This aldehyde was reacted under the conditions described in Example 1 changing methanol or butanol. The crude product was purified on a Sephadex LH-20 column (87.5×2.5 cm) using heptane:chloroform:ethanol, 20:20:1, as mobile phase. The fraction 610-674 ml was collected, evaporated and precipitated from methylene chloride—petroleum ether giving 76 mg of butyl (22R)-16α,17α-butylidenedioxy-6α,9α-difluoro-11β-hydroxy-3,20-dioxopregna-1, 4-diene-21oate. The purity determined by HPLC was 97.0%. Melting point: 185°-188° C. [α]D25= +63.3° (c=0.300; CH2Cl2) The molecular weight was 536.

EXAMPLE 7

To a solution of 185 mg of (22R)-16α,17α-butylidenedioxy-6α,9α-difluoro-11β-hydroxy-3, 20-dioxopregna-1,4-diene-21-al methyl hemiacetal in 10 ml of dimethylformamide was added 40 mg of potassium cyanide and 0.2 ml of glacial acetic acid. After stirring for 15 min. 0.5 g of manganese (IV) oxide was added. The reaction mixture was stirred at room temperature for another 2 h. The manganese (IV) oxide was removed by filtration and the residue was poured into 50 ml of water and thoroughly extracted with ethyl acetate.

The aqueous solution was acidified with hydrochloric acid and extracted with ethyl acetate. The extract was dried and evaporated. The residue was purified by chromatography on a Sephadex LH-20 column (88×2.5 cm) using chloroform: ethanol:glacial acetic acid, 95:5:0.25 as mobile phase. The fraction 985–1125 ml was collected and evaporated yielding 60 mg of (22R)-16α,17α-butylidenedioxy-6α,9α-difluoro-11β-hydroxy-3, 20-dioxopregna-1,4-diene-21-oic acid. The purity determined by HPLC was 99.0%. Mass spectrum (chemical ionization): 481 (MH+), 460 (MH+—HF), 409 (MH+—(CO$_2$)$_2$O).

EXAMPLE 8

To 680 mg of AgNO$_3$ dissolved in 1.2 ml of water was added 4 ml of 2M sodium hydroxide with stirring. The supernatant was centrifuged after 15 min. and the solvent decanted. The Ag$_2$O formed was suspended in 3 ml of 0.01M sodium hydroxide and 185 mg of (22R)-16α,17α-butylidnenedioxy-6α, 9α-difluoro-11β-hydroxy-3,20-dioxopregna-1,4-diene-21-al methyl hemiacetal was added. The suspension was stirred at room temperature for 1 h, centrifuged and the supernatant suspended in 3 ml of 0.01M sodium hydroxide and centrifuged three times. The combined alkaline phases were extracted with methylene chloride, acidified with 2M hydrochloric acid and extracted with ethyl acetate. The solvent was evaporated and the residue purified by chromatography on a Sephadex LH-20 column (88×2.5 cm) with chloroform:ethanol:glacial acetic acid, 95:5:0.25 as mobile phase. The fraction 900–1010 ml was collected and evaporated yielding 85 mg of (22R)-16α,17α-butylidenedioxy-6α,9α-difluoro-11β-hydroxy-3, 20-dioxopregna-1,4-diene-21-oic acid.

EXAMPLE 9

To a solution of 130 mg of (22R)-16α,17α-butylidenedioxy-6α,9α-difluoro-11β-hydroxy-3, 20-dioxopregna-1,4-diene-21-al methyl hemiacetal in 1.5 ml of acetone was added 3 ml of 0.1M aqueous Na$_3$PO$_4$ and 1 mg of potassium cyanide. The reaction mixture was stirred at room temperature for 30 min. Methylene blue (1% in water) was added dropwise until the colour remained. The reaction mixture was stirred for another 30 min., concentrated to ~2 ml and 25 ml of saturated aqueous NaHCO$_3$ was added. The mixture was washed with methylene chloride, acidified with 2M hydrochloric acid and extracted with ethyl acetate. The extract was dried and evaporated and the residue purified by chromatography on a Sephadex LH-20 column (88×2.5 cm) using chloroform:ethanol:glacial acetic acid 95:5:0.25 as mobile phase. The fraction 900–1005 ml was collected and evaporated yielding 27 mg of (22R)-16α,17α-butylidenedioxy-6α,9α-difluoro-11α-hydroxy-3, 20-dioxopregna-1,4-diene-21-oic acid.

EXAMPLE 10

To a solution of 100 mg of (22R)-16α,17α-butylidenedioxy-6α, 9α-difluoro-11β-hydroxy-3,20-dioxopregna-1, 4-diene-21-oic acid and 35 mg of potassium hydrogen carbonate in 10 ml of dimethylformamide was added 285 mg of methyl iodide. The reaction mixture was stirred at room temperature overnight, 50 ml of water was added and the mixture extracted with methylene chloride. The organic phase was separated, washed with 10 ml of saturated aqueous sodium thiosulphate, 2×10 ml of water, dried and evaporated. The residue was purified by chromatography on a Sephadex LH-20 column (72×6.3 cm) with chloroform as mobile phase. The fraction 2115–2550 ml was collected and evaporated. The residue was dissolved in methylene chloride and precipitated with petroleum ether (b.p. 40°–60° C.) yielding 88 mg of methyl (22R)-16α,17α-butylidenedioxy-6α, 9α-difluoro-11β-hydroxy-3,20-dioxopregna-1,4-diene-21-oate. The purity determined by HPLC was 96.2%. Melting point: 227°–35° C. The molecular weight was 494.

EXAMPLE 11

To a solution of 100 mg of (22R)-16α,17α-butylidenedioxy-6α, 9α-difluoro-11β-hydroxy-3,20-dioxopregna-1,4-diene-21-oic acid in 10 ml of dimethylformamide was added 0.2 ml of triethylamine and 0.5 ml of methyl iodide. The reaction mixture was stirred at 45° C. for 4 h, cooled to room temperature, diluted with 50 ml of methylene chloride, washed with water, dried and evaporated. The residue was purified by chromatography on a Sephadex LH-20 column (88×2.5 cm) using chloroform:ethanol:glacial acetic acid, 95:5:0.25 as mobile phase. The fraction 265–320 ml was collected and evaporated and the residue was precipitated from methylene chloride-petroleum ether (b.p. 40°–60° C.) yielding 89 mg of methyl (22R)-16α,17α-butylidenedioxy-6α, 9α-difluoro-11β-hydroxy-3,20-dioxopregna-1,4-diene-21-oate. The purity determined by HPLC was 98.8%. Melting point: 231°–36° C. The molecular weight was 494.

EXAMPLE 12

To a solution of 100 mg of (22R)-16α,17α-butylidenedioxy-6α, 9α-difluoro-11β-hydroxy-3,20-dioxopregna-1,4-diene-21-oic acid in 15 ml of benzene was added 65 ml of 1,5-diazabicyclo[5.4.0]undecene-5 and 0.5 ml of methyl iodide. The reaction mixture was stirred at 50° C. for 4 h, diluted with 50 ml of methylene chloride, washed with water, dried and evaporated. The residue was purified on a Sephadex LH-20 column (88×2.5 cm) with chloroform:ethanol:glacial acetic acid, 95:5:0.25, as mobile phase. The fraction 295–335 ml was collected and evaporated. The residue was dissolved in methylene chloride and precipitated with petroleum ether (b.p. 40°–60° C.) yielding 93 mg of methyl (22R)-16α,17α-butylidenedioxy-6α, 9α-difluoro-11β-hydroxy-3,20-dioxopregna-1,4-diene-21-oate. The purity determined by HPLC was 98.9%. Melting point: 231°–36° C. The molecular weight was 494.

EXAMPLE 13

(22R)-16α,17α-Butylidenedioxy-6α,9α-difluoro-11β-hydroxy-3,20-dioxopregna-1, 4-diene-21-oic acid (100 mg) and tetrabutylammonium hydrogen sulphate (100 mg) were added to 0.5 ml of 1M sodium hydroxide. A solution of 0.5 ml of methyl iodide in 10 ml of methylene chloride was added. The mixture was refluxed with stirring overnight. After cooling, another 20 ml of methylene chloride was added. The two layers were separated. The organic layer was washed with 2×10 ml of water, dried and evaporated. The crude product was purified by chromatography on a Sephadex LH-20 column (72×6.3 cm) using chloroform as mobile phase. The fraction 2130–2550 ml was collected and evaporated and the residue precipitated from methylene chloride-petroleum ether (b.p. 40°-60° C.) yielding 106 mg of methyl (22R)-16α,17α-butylidenedioxy-6α,9α-difluoro-11β-hydroxy-3, 20-dioxopregna-1,4-diene-21-oate. The purity determined by HPLC was 93.9%. Melting pint: 225°-35° C. The molecular weight was 494.

EXAMPLE 14

(22R)-16α,17α-Butylidenedioxy-6α,9α-difluoro-11β-hydroxy-3, 20-dioxopregna-1,4-diene-21-oic acid (100 mg) and 80 mg of tricaprylmethylammonium chloride (Aliquat 336) were added to 2.5 ml of saturated aqueous NaHCO₃. A solution of 0.5 ml of methyl iodide in 10 ml of methylene chloride was added. The mixture was stirred at 45° C. for 20 h, cooled and diluated with 20 ml of methylene chloride. The two layers were separated. The organic layer was washed with 3×5 ml of water, dried and evaporated. The crude product was purified by chromatography on a Sephadex LH-20 column (88×2.5 cm) with chloroform:ethanol:glacial acetic acid, 95:5:0.25, as mobile phase. The fraction 300-350 ml was collected and evaporated and the residue precipitated from methylene chloride-petroleum ether (b.p. 40°-60° C.) yielding 28 mg of methyl (22R)-16α,17α-butylidenedioxy-6α, 9α-difluoro-11β-hydroxy-3,20-dioxopregna-1,4-diene-21-oate. The purity determined by HPLC was 98.7%. Melting point: 231°-236° C. The molecular weight was 494.

EXAMPLE 15

(22R)-16α,17α-Butylidenedioxy-6α,9α-difluoro-11β-hydroxy-3, 20-dioxopregna-1,4-diene-21-oic acid (100 mg) was dissolved in 5 ml of methylene chloride and mixed with 5 ml of ethereal diazomethane solution. After 10 min, acetic acid was added dropwise, until the yellow colouring had disappeared. The mixture was evaporated and the residue dissolved in methylene chloride and precipitated with petroleum ether (b.p. 40°-60° C.) yielding 76 mg of methyl (22R)-16α,17α-butylidenedioxy-6α,9α-difluoro-11β-hydroxy-3, 20-dioxopregna-1,4-diene-21-oate. The purity determined by HPLC was 96.7%. Melting point: 228°-35° C. The molecular weight was 494.

EXAMPLE 16

To a solution of 82 mg of (22R)-16α,17α-butylidenedioxy-6α, 9α-difluoro-11β-hydroxy-3,20-dioxopregna-1,4-diene-21-al methyl hemiacetal in 25 ml of methanol, cooled in an ice-bath was added 0.06 ml of glacial acetic acid and then slowly 0.5 ml of 2M aqueous sodium hypochlorite with stirring. The reaction mixture was stirred for another hour. Methylene chloride (150 ml) was added and the solution was washed with 10% aqueous potassium carbonate and saturated sodium chloride. The organic phase was dried and evaporated. The residue was dissolved in methylene chloride and precipitated with petroleum ether (b.p. 40°-60° C.) yielding 9 mg of methyl (22R)-16α,17α-butylidenedioxy-6α,9α-difluoro-11β-hydroxy-3, 20-dioxopregna-1,4-diene-21-oate. The purity determined by HPLC was 93.8%. Melting point: 225°-35° C. The molecular weight was 494.

EXAMPLE 17

To a solution of 100 mg of methyl (22R)-16α,17α-butylidenedioxy-6α, 9α-difluoro-11β-hydroxy-3,20-dioxopregna-1,4-diene-21-oate in 12 ml of n-propanol was added 20 mg of potassium tert.-butylate. The reaction mixture was refluxed under argon protection for 1 h, cooled, poured into 25 ml of ice-water and extracted with methylene chloride. The extract was washed with saturated aqueous sodium hydrogen carbonate, dried and evaporated yielding 28 mg of propyl (22R)-16α,17α-butylidenedioxy-6α, 9α-difluoro-11β-hydroxy-3,20-dioxopregna-1,4-diene-21-oate. The purity determined by HPLC was 99.2%. Melting point: 262°-70° C. The molecular weight was 566.

EXAMPLE 18

Pharmaceutical Preparations

The following non-limitative examples illustrate formulations intended for different topical forms of administration. The amount of active steroid in the percutaneous formulations are ordinarily 0.001-0.2% (w/w), preferably 0.01-0.1% (w/w).

| Formulation 1, Ointment | |
|---|---|
| Steroid, micronized | 0.025 g |
| Liquid paraffin | 10.0 g |
| White soft paraffin ad | 100.0 g |
| Formulation 2, Ointment | |
| Steroid | 0.025 g |
| Propylene glycol | 5.0 g |
| Sorbitan sesquioleate | 5.0 g |
| Liquid paraffin | 10.0 g |
| White soft paraffin ad | 100.0 g |
| Formulation 3, Oil in water cream | |
| Steroid | 0.025 g |
| Cetanol | 5.0 g |
| Glyceryl monostearate | 5.0 g |
| Liquid paraffin | 10.0 g |
| Cetomacrogol 1000 | 2.0 g |
| Citric acid | 0.1 g |
| Sodium citrate | 0.2 g |
| Propylene glycol | 35.0 g |
| Water ad | 100.0 g |
| Formulation 4, Oil in water cream | |
| Steroid, micronized | 0.025 g |
| White soft paraffin | 15.0 g |
| Liquid paraffin | 5.0 g |
| Cetanol | 5.0 g |
| Sorbimacrogol stearate | 2.0 g |
| Sorbitan monostearate | 0.5 g |
| Sorbic acid | 0.2 g |
| Citric acid | 0.1 g |
| Sodium citrate | 0.2 g |
| Water ad | 100.0 g |
| Formulation 5, Water in oil cream | |
| Steroid | 0.025 g |
| White soft paraffin | 35.0 g |
| Liquid paraffin | 5.0 g |
| Sorbitan sesquioleate | 5.0 g |
| Sorbic acid | 0.2 g |
| Citric acid | 0.1 g |
| Sodium citrate | 0.2 g |
| Water ad | 100.0 g |
| Formulation 6, Lotion | |
| Steroid | 0.25 mg |
| Isopropanol | 0.5 ml |
| Carboxyvinylpolymer | 3 mg |
| NaOH | q.s |
| Water ad | 1.0 g |
| Formulation 7, Suspension for injection | |
| Steroid, micronized | 0.05-10 mg |
| Sodium carboxymethylcellulose | 7 mg |
| NaCl | 7 mg |
| Polyoxyethylene (20) sorbitan monooleate | 0.5 mg |
| Phenyl carbinol | 8 mg |
| Water, sterile ad | 1.0 ml |
| Formulation 8, Aerosol for oral and nasal inhalation | |
| Steroid, micronized | 0.1% w/w |
| Sorbitan trioleate | 0.7% w/w |

| -continued | |
|---|---|
| Trichlorofluoromethane | 24.8% w/w |
| Dichlorotetrafluoromethane | 24.8% w/w |
| Dichlorodifluoromethane | 49.6% w/w |
| Formulation 9, Solution for atomization | |
| Steroid | 7.0 mg |
| Propylene glycol | 5.0 g |
| Water ad | 10.0 g |
| Formulation 10, Powder for inhalation | |
| A gelatin capsule is filled with a mixture of | |
| Steroid, micronized | 0.1 mg |
| Lactose | 20 mg |

The powder is inhaled by means of an inhalation device.

PHARMACOLOGY

Anti-inflammatory effect

The selectivity for anti-inflammatory effect at the application site in the lung has been investigated in a model system in the rat after intrabronchial instillation of the glucocorticosteroid.

Instillation of Sephadex beads into rat lung leads to bronchial and alveolar inflammation. This provokes interstitial lung edema, which increases the lung weight and the inflammation can be graded as the increase of the lung weight compared to a vehicle-instilled control group. The lung edema formation can be counteracted by pretreatment with glucocorticosteroids, preferably the local administration as intrabronchial installation or as inhalation. Ideally, an anti-inflammatory action should be obtained only at the site of glucocorticosteroid application in the lung but not outside this area, as this in long term treatment can lead to therapy limiting systemic side effects.

The differentiation between glucocorticosteroid action in the treated lung region and outside this area has been tested by the following test protocol. Sprague-Dawley rats (225 g) were slightly anesthetized with ether and the glucocorticosteroid test preparation in a volume of 0.5 ml/kg was instilled into just the left lung lobe. This was achieved by instillation with a thin and bent steel catheter applied via the mouth and trachea into the left lung lobe (the selectivity of this mode of application into just the left lobe has been verified by separate experiments with Evans Blue, when it was found that >95% of applied substance was found in the left and <5% in the right lung half). Thirty minutes later, a suspension of Sephadex (5 mg/kg in a volume of 1 ml/kg) was instilled in the trachea well above the bifurcation so that the suspension reached both the left and right lung lobes. Twenty hours later the rats were killed and the left and right lung lobes were dissected out and weighed separately. Also the thymus weight was recorded. Control groups got vehicle instead of glucocorticosteroid preparation and saline instead of Sephadex suspension to determine the weight of non-drug protected Sephadex edema and the normal lung weight, respectively. For each glucocorticosteroid preparation at least 3 doses within the range 0.01–10 mg/kg and with each $\geq 6$ parallels/dose were tested. The glucocorticosteroids were suspended in a vehicle of CMC-Na 0.75%, Tween 80 0.04%, and 0.7% NaCl ad 100%.

For a strict local anti-inflammatory treatment of airway diseases the ideal profile of a compound is that it should counteract the inflammation in the locally treated left lung lobe, but not in the right lung half, which is anticipated to be reached by glucocorticosteroid first via the systemic circulation (after absorption from the left lung). The ratio between the required $ED_{50}$'s (doses reducing the edema by 50%) in the right and left lung halves, respectively, can be used as a parameter for estimation of the selective activity for the application site. For an ideal glucocorticosteroid this selectivity ratio should be high.

The results of the performed tests are given in Table 1, where the upper part represents effects reached by earlier known types of glucocorticosteroids. Budesonide does not reach any selectivity for the application site in lung, as the required $ED_{50}$'s for the left and right lung halves were rather similar (selectivity ratio ~1.5). At the highest tested dose (0.3 mg/kg) budesonide reduces the thymus weight by 22% (p<0.01). The earlier known glucocorticosteroid FCB reaches some selectivity as reduction of the edema of the right lung half requires an about 2–3 times higher dose than the necessary dose to inhibit the left lung edema.

The new compounds according to the invention show surprisingly a much better selectivity for activity just in the locally treated left lung lobe (Table 1). The selectivity ratio reaches 6 or even higher figures. With these compounds it is possible to inhibit the edema of the left lung by at least 60% without any significant effects on the edema of the right lung half. At the dose 10 mg/kg the compounds according to examples 1 and 5 do not at all affect the thymus weight, while the compound according to example 3 at the same dose induces a slight reduction of thymus weight (by 15%, p<0.05).

The new compounds have all a higher anti-inflammatory potency at the application site ($ED_{50}$ value in the left lung lobe $\leq 5$ mg/kg) than the low potency demonstrated for FCB (10 mg/kg).

TABLE 1

Effects of tested glucocorticosteroids in the Sephadex model. The results are given in relation to the corresponding control group given Sephadex.

| Compound according to Example | $ED_{50}$* left lung lobe mg/kg | Selectivity ratio $ED_{50}$* right lung / $ED_{50}$* left lung | Thymus involution % (dose mg/kg) |
|---|---|---|---|
| Budesonide | 0.2 | 1.4 | 22 (0.3) |
| FCB | 10 | 2.5 | 6 (10) |
| 1 | 1.5 | 6.0 | −3 (10) |
| 3 | 1.7 | 5.9 | 15 (10) |
| 5 | 5 | 10.0 | −1 (10) |
| 4 | <1 | >10 | 6 (10) |

*$ED_{50}$ = required glucocorticosteroid dose to reduce the edema by 50%.

We claim:

1. A compound of the formula

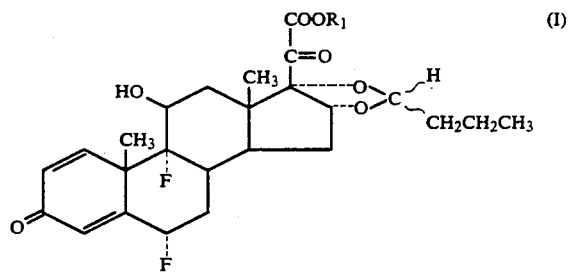

or a stereoisometric component thereof, in which formula $R_1$ is selected from a straight or branched hydrocarbon chain having 1–4 carbon atoms.

2. A compound according to claim 1 wherein $R_1$ is a methyl group.

3. A compound according to claim 1 wherein $R_1$ is an ethyl group.

4. A compound according to claim 1 wherein $R_1$ is a n-propyl group.

5. A compound according to claim 1 wherein $R_1$ is an isopropyl group.

6. A compound according to claim 1 wherein $R_1$ is a n-butyl group.

7. A pharmaceutical preparation comprising as active ingredient a compound according to claim 1 in association with a pharmaceutically acceptable carrier.

8. A pharmaceutical preparation according to claim 7 in dosage unit form.

9. A method for treatment and control of inflammatory or allergic conditions *of mucosae* in mammals, which comprises administering to a host in need of such treatment an effective amount of a compound according to claim 1.

10. A method according to claim 9 wherein the inflammatory or allergic condition is associated with rhinitis or asthma.

* * * * *

UNITED STATES PATENT AND TRADEMARK OFFICE
CERTIFICATE OF CORRECTION

PATENT NO. : 5,215,979
DATED : June 1, 1993
INVENTOR(S) : Andersson et al.

It is certified that error appears in the above-indentified patent and that said Letters Patent is hereby corrected as shown below:

col. 1, line 25, change "thinitis" to --rhinitis--;

col. 1, line 34, change "side" to --wide--;

col. 1, lines 42, change "Brattand" to --Brattsand--;

col. 2, line 42, change "steroic" to --steroid--;

col. 4, line 19, change "ozides" to --oxides--;

col. 4, line 43, and col. 5, line 26, change "soluene" to --toluene--;

col. 4, line 53, change "minimum" to --minium--;

col. 4, line 58, change "suitable" to --suitably--;

col. 7, line 61, change "therodynamic" to --thermodynamic--;

col. 8, line 58, delete "moved;"

col. 8, line 67; col. 9, line 59; col. 10, line 13; col. 10, line 37; col. 10, line 59, change "$[\alpha]D25$" to --$[\alpha]_D^{25}$--;

col. 9, line 31, change "Sephanex" to --Sephadex--;

UNITED STATES PATENT AND TRADEMARK OFFICE
CERTIFICATE OF CORRECTION

PATENT NO. : 5,215,979
DATED : June 1, 1993
INVENTOR(S) : Andersson et al.

It is certified that error appears in the above-indentified patent and that said Letters Patent is hereby corrected as shown below:

col. 9, line 45 and col. 10, line 18, change "as" to --was--;

col. 10, line 31, change "the" to --and--;

col. 10, line 50, change "or" to --for--;

col. 11, line 24, change "butylidnenedioxy" to --butylidenedioxy--;

col. 11, line 58, change "11α" to -- 11β --;

col. 13, line 5, change "pint" to --point--;

col. 13, line 15, change "diluated" to --diluted--;

col. 16, line 65, change "stereoisometric" to --stereoisomeric--;

Signed and Sealed this

Tenth Day of February, 1998

Attest:

BRUCE LEHMAN

*Attesting Officer*     *Commissioner of Patents and Trademarks*